US00PP10285P

United States Patent [19]

Zaiger et al.

[11] Patent Number: Plant 10,285

[45] Date of Patent: Mar. 17, 1998

[54] INTERSPECIFIC TREE "FLAVOROSA"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 782,078

[22] Filed: Jan. 13, 1997

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of Interspecific tree [(*Prunus salicina*×(*Prunus salicina*×*Prunus armeniaca*)] which has the following unique combination of desirable features:

1. Heavy and regular production of fruit.
2. Fruit with excellent flavor and eating quality.
3. Early maturity of fruit.
4. Large tree size with vigorous, upright growth.
5. Precocious production of fruit, usually producing fruit in the second year after planting.
6. Fruit with an attractive blackish, violet skin color.
7. Fruit with firm flesh and good shipping quality.

1 Drawing Sheet

ORIGIN OF THE VARIETY

The new and distinct variety of interspecific tree was originated by us in our experimental orchard located near Modesto, Calif., as a first generation cross between two seedling selections with field identification numbers 65EC664 and 42GA580. The maternal parent (65EC664) originated from an open pollinated Royal Zee Plum (U.S. Plant Pat. No. 5,486) seed. The paternal parent (42GA580), which is a plum cot, originated as a seedling selection from a seed of an open pollinated Red Beaut Plum (U.S. Plant Pat. No. 2,539) tree that had been grown from budwood which had been irradiated with cobalt. The new interspecific variety was selected from a large group of first generation seedlings which were grown and maintained by us, one such seedling having especially desirable fruit characteristics was selected for asexual reproduction and commercialization.

ASEXUAL REPRODUCTION OF THE VARIETY

Asexual reproduction of the new and distinct variety of interspecific tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

A new and distinct variety of interspecific tree (plum× plum cot) which is of large size, vigorous, upright growth; and a heavy and productive bearer of large, clingstone fruit with excellent flavor and eating quality. Further characterized to its novelty is its firm, dark ruby red flesh; having a good balance between sugar and acid with an average Brix of 16°; having good handling and shipping quality; and having an attractive blackish, violet skin color. In comparison to the interspecific variety Flavor Supreme (U.S. Plant Pat. No. 6,763), the new variety has darker flesh and skin color, is flatter in shape and is approximately 19 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Usually pruned to vase shape.
- *Productivity.*—Productive.
- *Bearer.*—Regular.
- *Density.*—Medium.
- *Growth.*—Upright.

Trunk:
- *Size.*—Large, medium stocky.
- *Texture.*'Shaggy.
- *Color.*—Brown to dark brown (6-E-7) to (6-E-8).

Branches:
- *Size.*—Medium.
- *Texture.*—Smooth to medium rough, varies with age of growth.
- *Lenticels.*—Medium number. Small in size.
- *Color.*—Light brown to brown (5-D-6) to (5-E-7), varies with age of growth.

Leaves:
- *Size.*—Large. Average length 4½". Average width 1½".
- *Form.*—Oblanceolate, pointed.
- *Margin.*—Finely serrate.
- *Thickness.*—Medium.
- *Surface.*—Smooth.
- *Petiole.*—Average length ⅝". Average width 1/16".
- *Glands.*—Number varies from 1 to 4. Average number 3. Medium in size. Globose. Located on upper portion of petiole and lower portion of leaf blade.

*Color.*—Upper surface—green to dark green (27-F-6) to (27-F-8). Lower surface—light green to grayish green (27-E-5) to (27-E-6).

Flower buds:

*Size.*—Medium.

*Length.*—Medium.

*Form.*—Plump.

Flowers:

*Size.*—Medium.

*Pollen.*—Present.

*Blooming period.*—Date of first bloom: Feb. 13, 1996. Date of last bloom: Feb. 19, 1996. Varies slightly with climatic conditions.

*Color.*—White.

Fruit:

*Maturity when described.*—Firm ripe.

*Date of first picking.*—May 24, 1996.

*Date of last picking.*—May 30, 1996. Varies slightly with climatic conditions.

*Size.*—Medium to large. Average diameter axially 2". Average transversely in suture plane 2½".

*Form.*—Oblate.

*Suture.*—Very shallow, extends from base to apex.

*Ventral surface.*—Rounded.

*Apex.*—Retuse.

*Base.*—Retuse.

*Cavity.*—Rounded, small, slightly elongated in suture plane. Average depth ⅜". Average breadth 7/16".

Flesh:

*Ripens.*—Evenly.

*Texture.*—Firm.

*Fibers.*—Small, tender.

*Aroma.*—Moderate.

*Amygdalin.*—Undetected.

*Eating quality.*—Excellent.

*Flavor.*—Excellent.

*Color.*—Varies from dark ruby red to dark magenta (11-F-8) to (12-F-7). Pit cavity slightly darker magenta (12-F-8).

Skin:

*Thickness.*—Medium.

*Texture.*—Medium tough, tenacious to the flesh.

*Bloom.*—Moderate.

*Tendency to crack.*—None.

*Color.*—Grayish magenta ground color (14-E-5) showing as small dots near apex on some fruit, overspread with egg plant to blackish violet (14-F-3) to (15-F-4).

Stone:

*Type.*—Clingstone.

*Size.*—Medium. Average length ⅝". Average width ⅞". Average thickness ½".

*Form.*—Obovoid.

*Base.*—Straight.

*Apex.*—Usually cuspidate, varies from cuspidate to acuminate.

*Surface.*—Grooved toward apex, usually one long groove on each side of suture plane. Small narrow ridges throughout, some extending from base to apex, others very short. Very lightly pitted throughout.

*Sides.*—Equal to unequal, both sides extend outward becoming winged, creating greater width than length to stone.

*Tendency to split.*—None.

*Color.*—Light brown to brown (5-D-4) to (5-E-6).

Use: Dessert. Market, local and long distance.

Keeping quality: Good.

Shipping quality: Good.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific (plum×plum cot) tree, substantially as illustrated and described, characterized by its large size, vigorous, upright growth and a productive and regular bearer of early maturing fruit with excellent flavor and eating quality; the fruit is further characterized by having firm, dark ruby red flesh with good handling and shipping quality and, in comparison to the interspecific variety Flavor Supreme (U.S. Plant Pat. No. 6,763), the new variety is flatter in shape and is approximately 19 days earlier in maturity.

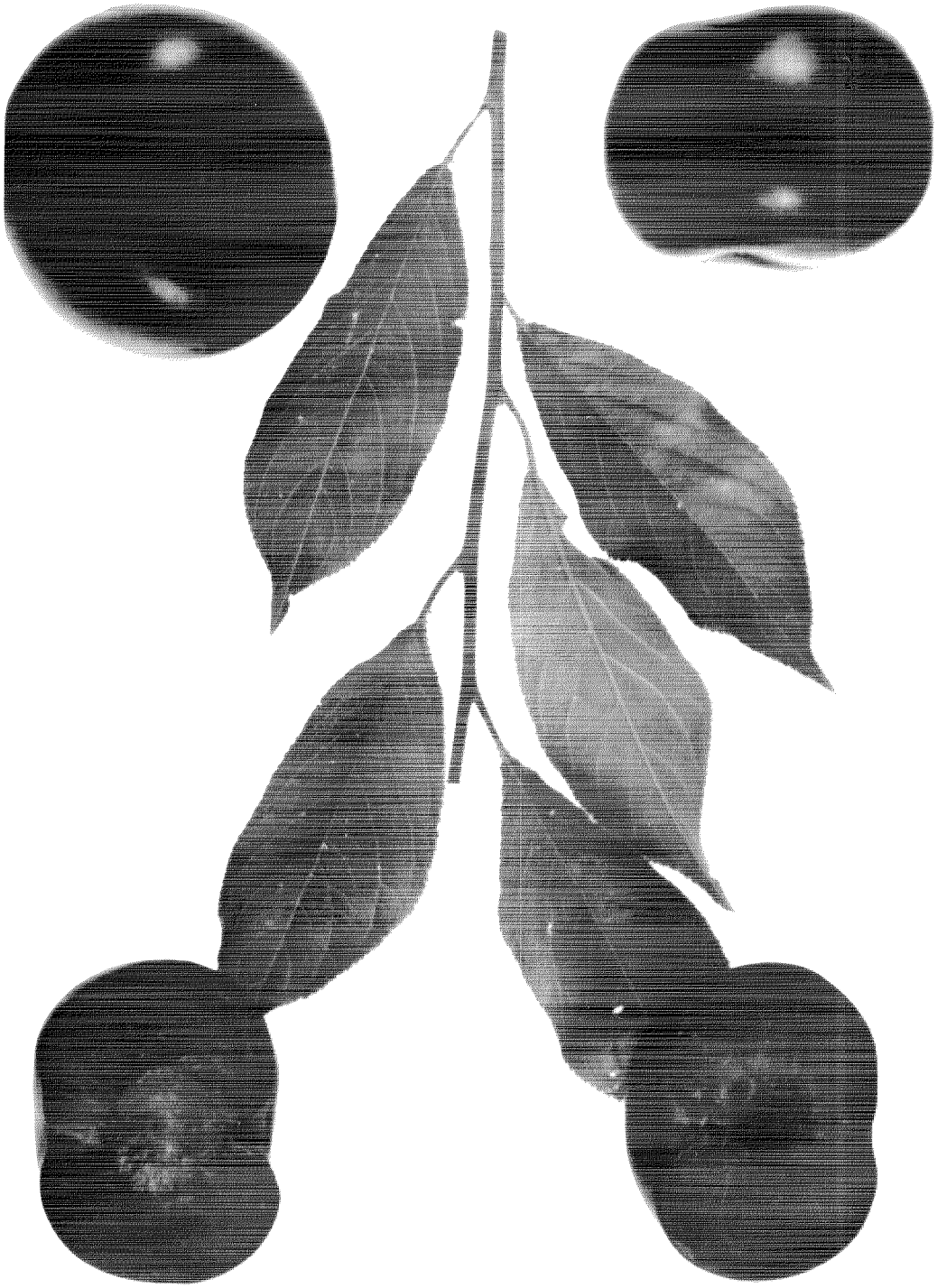

* * * * *